United States Patent [19]

Weissman

[11] Patent Number: 4,885,965

[45] Date of Patent: * Dec. 12, 1989

[54] ROTARY SAW FOR SECTIONING DENTAL MODELS

[75] Inventor: Bernard Weissman, New York, N.Y.

[73] Assignee: IPCO Corporation, White Plains, N.Y.

[*] Notice: The portion of the term of this patent subsequent to Apr. 4, 2006 has been disclaimed.

[21] Appl. No.: 234,301

[22] Filed: Aug. 19, 1988

Related U.S. Application Data

[63] Continuation of Ser. No. 14,662, Feb. 13, 1987, Pat. No. 4,817,839.

[51] Int. Cl.$^4$ .............................................. B26D 7/18
[52] U.S. Cl. ........................................ 83/100; 83/474; 83/477.2; 83/520; 83/DIG. 1; 225/96
[58] Field of Search ................... 83/51, 100, 437, 471, 83/474, 477.2, 478, 520, 571, 862-864, 872-875, DIG. 1, 446, 447, 431, 570, 861; 76/DIG. 12; 29/160.6; 225/96

[56] References Cited

U.S. PATENT DOCUMENTS

| | | | |
|---|---|---|---|
| 2,806,492 | 9/1957 | Becker | 83/520 |
| 2,930,418 | 3/1960 | Moore | 83/477.2 X |
| 4,070,941 | 1/1978 | Lorenz | 83/DIG 1 X |
| 4,144,781 | 3/1979 | Kreitz | 83/100 |
| 4,169,400 | 10/1979 | Ducret | 83/477.2 X |
| 4,379,418 | 4/1983 | Martin | 83/DIG. 1 X |
| 4,533,812 | 8/1985 | Lorenz | 76/DIG. 12 X |
| 4,817,839 | 4/1989 | Weissman | 225/2 |

Primary Examiner—Frank T. Yost
Assistant Examiner—Rinaldi Rada
Attorney, Agent, or Firm—Helfgott & Karas

[57] ABSTRACT

A rotary table saw for sectioning dental models having a housing with a base portion and a working table mounted on the base portion. The working table is controllably depressible so as to be moved upward and downward with respect to the base. The motor housed in the base drives a rotary blade oriented in a vertical direction. A slit in the work table permits the blade to emerge therethrough as the work table is depressed. The vacuum outlet is placed in flow communication with the surface of the work table during depression of the work table to remove saw dust from the work table. The dental model is placed on the work table with the blade hidden beneath the work table. The work table is depressed to permit emerging of the rotary blade cutting from the underside of the dental model.

9 Claims, 3 Drawing Sheets

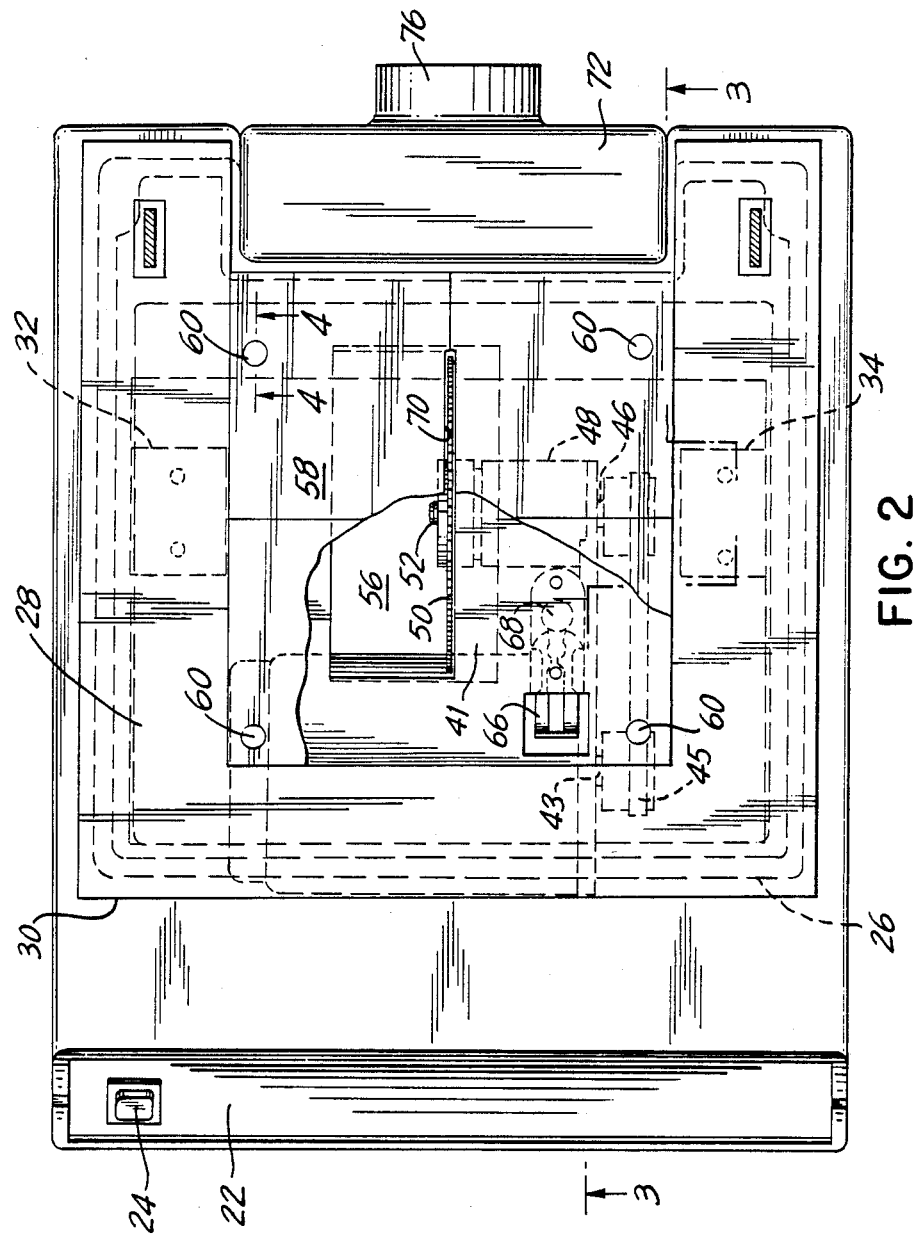

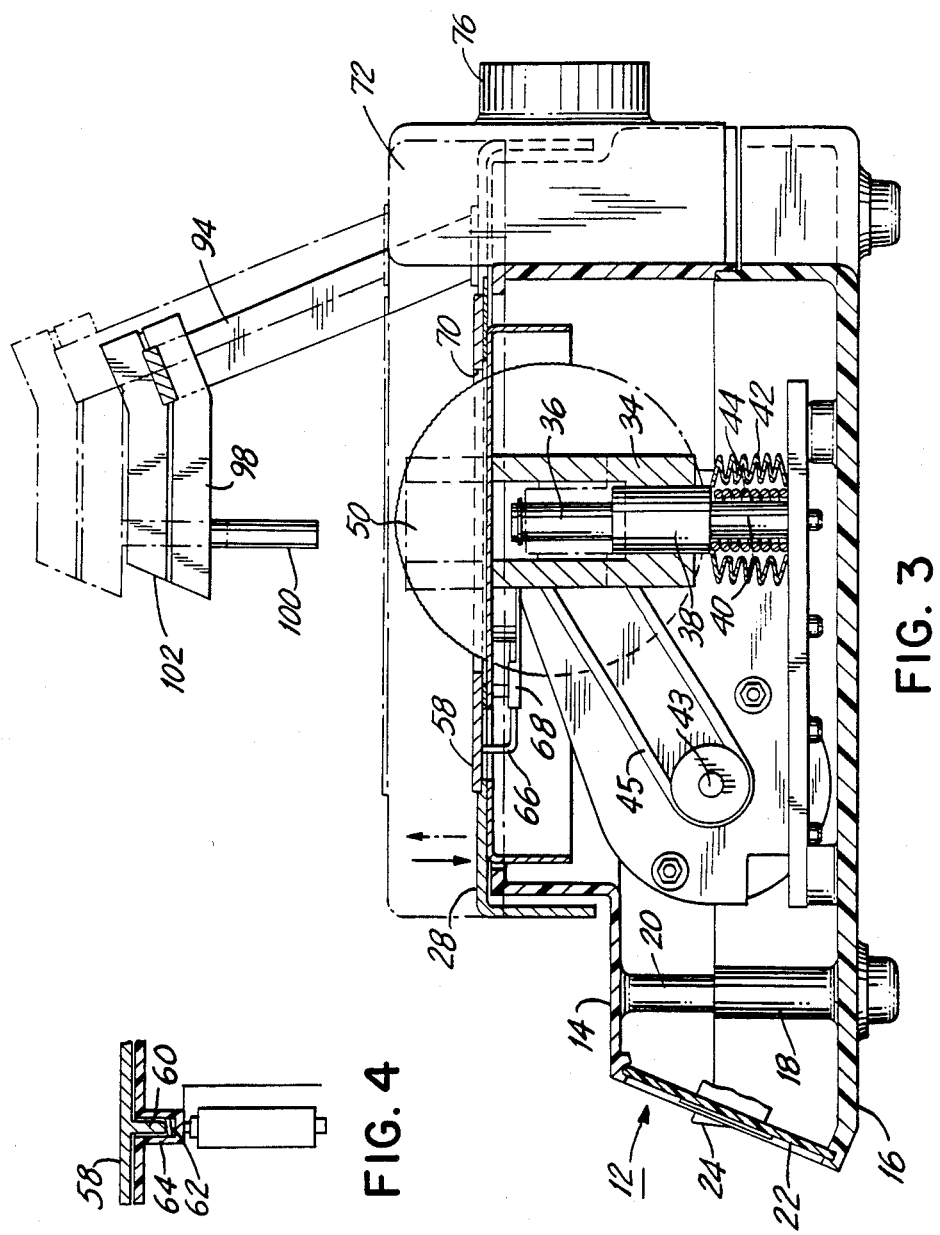

ROTARY SAW FOR SECTIONING DENTAL MODELS

This is a continuation application of Ser. No. 014,662, filed Feb. 13, 1987, now U.S. Pat. No. 4,817,839.

BACKGROUND OF THE INVENTION

This invention relates to dental apparatus and more particularly to a rotary table saw which can be used for segmenting sections of dental models.

In various dental procedures, a dental model is initially formed. After the model has been accurately formed, it is often necessary to segment the dental model into sections with each section having the capability of being returned to its original position into a dental tray or base. The segmenting must be done very carefully, in order to avoid damaging the marginal line which will occur where the restoration will join the natural portions of the mouth structure. In order to protect such margin, typically the dental models are cut by hand from their occlusal side.

In the cutting and segmenting of the model, initially a line is identified along which the cut should be made. Then, cutting with a thin blade, the dentist or technician will cut through from the occlusal side as far down as possible. He will then break off the segment after the cut has substantially passed through most of the dentition portion of the model.

Since the cuts are typically made by hand using a thin blade with a handsaw, numerous problems occur introducing inaccuracies in the cutting. For example, the saw may angle or bend along the way and the cut will not be perfectly straight. In fact, sometimes undercuts will occur whereby it will not be possible to replace that segment without further trimming and cutting down of important aspects of the dental model which would otherwise be preserved.

Also, the accuracy and repeatability of the cuts is difficult to achieve by hand.

Where automatic large rotary saws are utilized, dangerous situations may occur and the type of sawing which is achieved frequently causes breakage of the model itself. Typically, a horizontal rotary saw is utilized which rotates towards the operator. The operator holds the model in a fixture and then pushes the model in the fixture against the horizontal rotary saw.

Frequently the model may not be such that it can fit into a fixture for the particular segment that is being cut. As a result, the dentist or technician may actually try holding it by hand causing a further dangerous condition. During such operation, the dental model which is held by hand or in a fixture can break. Additionally, the toothed blade utilized in the saw can actually catch the dentist's hand causing a deep cut or gash.

The rotary blade which is utilized also presents a hazard. If the blade is covered and shielded prior to use, then the shield must be lifted as the dental model is brought against the saw. This causes awkwardness since the dental model must be held in only one hand and the shield removed with the other hand. Holding the model with only one hand is dangerous and may cause breakage of the model.

Where the rotary blade is fully exposed, while the model can be held with two hands, the exposed blade presents a hazard prior to its being used.

Prior to the present invention, dental models were segmented generally using a manual operation. Typically, after the dental model is completed, it is desirous to segment the model. Caution must be had to maintain the margin between the natural and artificial parts in a protected state. Accordingly, an initial indication is usually provided on the occlusal side of the teeth protecting the marginal area. A thin blade is then used to saw downward from the occlusal surface to the bottom, usually through all of the dental model and into the base. Either the sawing goes completely through the base, or the bottom is simply broken off.

Where a rotary saw is utilized, such rotary saws are usually of the type that rotate towards the operator. The operator holds the model in a fixture and presses the model against the saw. This is often difficult since the model may not always be of a type or shape that can be maintained in a fixture. As a result, it can fracture the model or the user is forced to hold the model by hand without a fixture. This is dangerous, especially when the blade is rotating toward the operator.

Additionally, when such a rotary blade is utilized, it is usually exposed. As a result, when the operator beings, the blade is already rotating and if the operator slips, the blade can cut into his hand.

If a protector were to be placed over such a rotary blade, it would be necessary for the user to lift the protector with one hand, leaving only the other hand for holding the model which is dangerous to hold the model with one hand while trying to saw it.

Accordingly, improvements are warranted in the type of rotary saw which is utilized for segmenting dental models so as to avoid hazards, improve the ability to cut and separate the model into segments, and improve the accuracy, repeatability, and other cutting functions not heretofore achievable with prior art devices.

SUMMARY OF THE INVENTION

Accordingly, it is an object of the present invention to provide a rotary blade saw for dental use which avoids the aforementioned problems of prior art devices.

Another object of the present invention is to provide a rotary dental saw which can provide improved segmenting of dental models.

A further object of the present invention is to provide a rotary saw lying in a vertical orientation with respect to a horizontal working table, whereby the model is supported on the horizontal surface during the cutting operation.

Still a further object of the present invention is to provide an apparatus which segments dental models by cutting the dental model from the underside.

A further object of the present invention is to provide a dental rotary table saw which has a working table supporting the dental model with the table being depressible so that as it is lowered a rotary blade becomes exposed for cutting the dental model from its underside.

Another object of the present invention is to provide a new method for segmenting dental models by identifying a cutting line on the occlusal side and then providing the cutting of the dental model from the underside of the model.

Briefly, in accordance with the present invention, there is provided a rotary table saw for sectioning dental models. The table saw includes a housing having a base portion. A motor is located in the base portion and drives a rotary blade with the blade being oriented in a vertical plane. A controllably depressible horizontal work table is mounted on the base portion and covers the blade in its normal position. The dental model is supported on the surface of the work table. A slit in the work table is available for admitting the rotary blade. As the table is lowered, the rotary blade is progressively exposed through the slit to project above the work table. The amount of the lowering of the work table can control the feeding amount of the blade. With the dental model placed on the work table, the blade cuts upwardly from the underside of the dental model. A vacuum outlet is coupled to the base portion so that as the work table is lowered the vacuum outlet is exposed thereby removing dust from the work table. The rotary table saw further includes an overhead beam light which is focused downwardly onto the work surface and is positioned to identify the diametric center of the rotary blade. This provides an exact indication of the location of the cut on the dental model placed on the working table.

The present invention also contemplates a new method of segmenting dental models including the steps of initially locating the desired cutting line on the model and then making an initial slight cut occlusally along the cutting line. The dental model is then placed on the horizontal work table and a rotary blade saws upwardly from the underside of the dental model until the cut approaches the occlusal side. If desired, the segment is then broken between the occlusal cut and the large saw cut from the underside.

In order to avoid harm to the user, the blade is a diamond impregnated coated blade without teeth or barbs.

The aforementioned objects, features and advantages of the invention will, in part, be pointed out with particularity, and will, in part, become obvious from the following more detailed description of the invention, taken in conjunction with the accompanying drawing, which forms an integral part thereof.

BRIEF DESCRIPTION OF THE DRAWINGS

In the drawings:

FIG. 2 is a plan view of the rotary saw looking down onto the work table with portions thereof being cut away to expose interior equipment;

FIG. 3 is a cross sectional view taken along lines 3—3 of FIG. 2; and

FIG. 4 is a cross sectional view taken along lines 4—4 of FIG. 2; and showing the interlock switch.

In various figures of the drawing, line reference characters designate like parts.

DESCRIPTION OF THE PREFERRED EMBODIMENT

Figure 1:
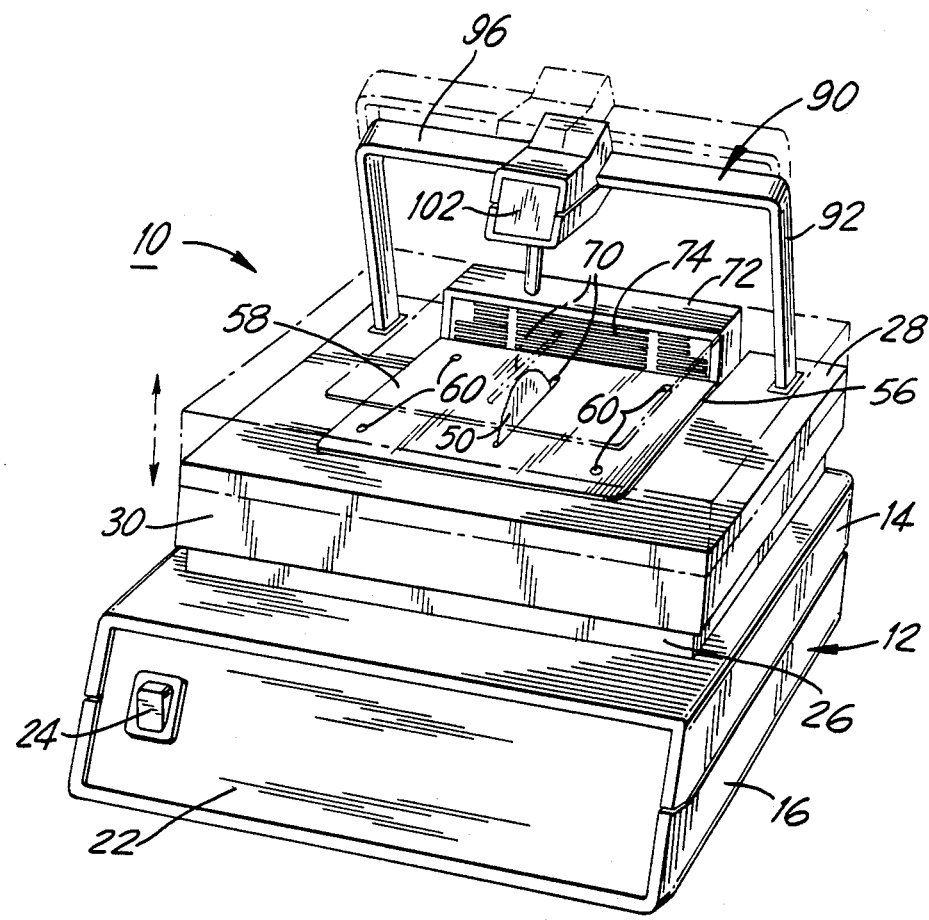
FIG. 1 is a perspective view of the rotary saw in accordance with the present invention showing in solid lines the work table in its lowered position and in dotted lines the work table in its upper, initial normal resting position.

Referring now to the figures, the rotary table saw is shown generally at 10 and includes a base 12 formed of upper and lower mating sections 14, 16 which interlock to form a composite base housing compartment. The lower section 16 includes receiving studs 18 for receiving downward projecting posts 20 of the upper section 14 of the base 12 to interconnect the sections in interlocking fashion. A front plate 22 interconnects the front of upper and lower sections 14, 16 of the base and supports a main switch 24 for turning on and off of the rotary saw.

Upwardly projecting from the upper section 14 of the base 12 is a pedestal wall 26 formed as rectangular outer peripheral wall. Sitting on this pedestal wall 26 is a work table 28 having downwardly depending skirt walls 30 peripherally thereabout. The skirt wall 30 is slightly spaced around the pedestal wall 26 to permit upward and downward movement of the work table with respect to the pedestal. A pair of linear bearings 32, 34 are provided for facilitating the upward and downward movement of the work table 28 with respect to the pedestal 26. The linear bearings include an inner piston 36 slidable within an outer sleeve 38. A lower depending shaft 40 extends from the sleeve 38 and is surrounded by a bellows 42. The bellows surrounds an inner spring 44 which provides automatic return movement when the work table 28 is depressed.

Within the interior of the apparatus, is included a motor 41 having an output shaft 43 to which is connected a rotary belt 45 which drives the output 46 of a bearings 48. The bearings in turn control the rotation of a vertically oriented saw blade 50. The saw blade is held in place by means of a nut 52 which can be loosened to remove the blade 50 for replacement.

An opening 56 is provided on the work table in which is inserted a working surface plate 58 held in place by four pins 60 in its corners. By insertion of a tool in the edge of opening 56, the plate 58 can be removed to gain access to the interior of the apparatus for maintenance of the various parts as well as replacement of the rotary saw blade.

As shown in FIG. 4, one of the pins 60 includes an interlock switch 62 embedded within the receptacle 64 into which it is situated such that upon removal of the plate 58, the motor is deenergized thereby stopping rotation of the saw.

Removal of the plate 58 exposes a hand latch 66 which can be forwardly slid into a receiving catch 68 to retain the work table 28 in its lowermost position. In this manner, for maintenance, the plate 58 is removed, the work table is depressed to its lowermost position and the latch 66 pressed forward to lock the table in its lower position. This facilitates direct access to the nut 52 holding the rotary blade in place and permits the blade to be easily removed and replaced.

A slit 70 is provided in the plate 58 so that the rotary saw blade 50 can extend upwardly through the slit as the work table is depressed. In its normal, uppermost position, however, as shown in the dotted line in FIG. 1, the blade is completely recessed beneath the work table and directly under the slit 70 in the plate 58. No part of the blade is exposed when the work table is in its upper most position. As the work table is depressed, the blade becomes exposed as it emerges upwardly through the slit above the top surface of the plate 58.

Positioned behind the plate 58 is an air chamber 72 having a grillwork 74 at its front. A vacuum outlet 76 is provided at its rear for connection to an air suction device. As shown in FIGS. 1 and 3, with the work table in its uppermost position, it is substantially flush with the top surface of the air housing 72. As the work table is depressed, the grillwork becomes visible and the suction provided at the grillwork can pull off any dust from the work table resulting from operation of the rotary saw.

The vacuum can either be coupled to the outlet port 76 or can be actually built into the apparatus and positioned within the chamber 72.

Supported from the work table 28 is an overhead bridge 90 comprising side arms 92, 94 and a cross arm 96. Depending from the cross arm 96 is a housing 98 from which depends a rod 100 through which a beam light 102 is emitted. The beam light is focused so that it is directly over the cutting point 102 at the diametric top of the rotary blade.

The beam light can also reflect through a forward plate providing a visual indication of the operation of the beam light.

Using the present apparatus, all of these problems are avoided. A desired location of a cut is marked on the occlusal surface. A slight cut may be provided to indicate the line along which the cut should be made.

The model is then placed on the top of the working table. At this point, with the working table in its upper most position, the blade is completely covered so that there is no chance of the operator cutting himself on any exposed blades. The model is placed so that the beam of light downwardly projecting from the overhead bridge is located directly at the point of the desired cut. While holding the model with two hands, the operator depresses the working table. The speed of depression can be controlled so that the feed of the saw as it becomes exposed through the slit in the plate can be likewise controlled. The operator continues depressing the working table so that the saw cuts upwardly through the base of the model and continues upwardly therefrom through the dental portion of the model itself. Typically, the sawing is stopped well before reaching the occlusal surface and the final separation is caused by breaking apart the section.

For added safety, the saw itself is formed as a rotary blade which is diamond impregnated and coated. It is formed without teeth or barbs and provides a fast, smooth and precise cut. Because of the ultrasmooth parallel cuts, it eliminates the need for additional finishing on the sides. At the same time, because of the absence of teeth, it avoids the possibility of catching the hand of the operator. Such type of blade would not have been used in a horizontal saw of the prior art type, since a tooth blade was required in order to get the cut started.

The apparatus of the present invention provides a fast and safe way to section models. It offers total visibility of the model as the light beam indicator pin points the exact location of the area to be cut. The blade is stored beneath the work surface when the unit is not in use. The cutting edge of the blade is only exposed when the operator depresses the work table with both hands during the cutting procedure. This allows the operator total control, convenience and safety.

Through the use of the horizontal work table and the vertical blade, the cutting disk will cut the model into desirable sections perpendicular to the model base. Thus, all cuts are parallel to each other, permitting the removal and re-seating of sections without interference. The emerging blade from the undersurface of the machine allows for safe positioning and sectioning of the models without the danger of injury to the model or pin-indexed dyes to operate and elevate the blade to the desired height of the cut. Both hands must hold the side of the model in place and thus provides safety against accidental injury to the operator.

The unique design of sectioning from the underside of the model provides safety against accident injury to the fine proximal contacts of dies and to adjacent teeth. It should be appreciated, that not only is there provided a unique apparatus, but the method of sectioning dental models is also unique as a result of the present apparatus. Heretofore, it was not the typical method to cut through the underside of the base of the dental model. It was typical to cut through from the occlusal side. Furthermore, it was not usual to hold the dental model in a horizontal position on a work table and cut through from the underside of the model. Accordingly, this entire approach is a novel method of sectioning dental models and brings about improved ability to achieve such sectioning with perfectly reproducible and parallel cuts.

Although the amount of depression of the work table can be individually controlled, it is also possible to incorporate a locking or latching system which limits movement to a specific height. In this way, uniform depth of cut can be controlled by providing a lock on the height so that each cut causes the table to move downward an identical amount.

There has been described therefore the best embodiments of the invention presently contemplated. However, should be understood that various changes and modifications may be made thereto without departing from the spirit of the invention.

I claim:

1. A rotary table saw for sectioning dental models, comprising:

a housing having a base portion, a motor housed in the base portion for driving a rotary blade oriented in a vertical plane, a controllable depressible horizontal work table mounted on the base portion covering the blade for freely supporting a dental model on its surface, control means responsive to the downward application of pressure on the work table for lowering the work table by a distance corresponding to the amount of pressure applied, a slit in said work table for progressively exposing said rotary blade through the work table as the work table is depressed for controlled feeding of the blade as the blade cuts upwardly through the underside of the dental model, and a vacuum outlet coupled to the base portion, the vacuum outlet being placed in flow communication with the surface of the work table during depression of the work table and transverse to the plane of the blade to remove the saw dust from the work table.

2. A rotary table saw as in claim 1, and further comprising an overhead beam light focused onto the diametric center of the rotary blade for identifying location of the cut.

3. A rotary table saw as in claim 1, and comprising an upstanding bridge supported on said work table, and a beam light depending from said bridge for identifying a location of the cut, whereby said beam light moves together with the work table to remain focused on the location of the cut.

4. A rotary table saw as in claim 1, and comprising a diamond impregnated, coated, rotary blade without teeth or barbs.

5. A rotary table saw as in claim 1, and comprising a removable top plate on said working table for providing access to the rotary blade for maintenance thereof.

6. A rotary table saw as in claim 1, and comprising linear bearings supporting said work table for permitting raising and lowering of the work table.

7. A rotary table saw as in claim 1, and comprising biasing means for retaining said table in a normally raised position covering the blade.

8. A rotary table saw as in claim 7, wherein said biasing means are springs, and comprising linear bearings supporting said work table, said springs surrounding said linear bearings.

9. A rotary table saw as in claim 8, and further comprising bellows surround said linear bearings and springs.

* * * * *